United States Patent [19]
Griffey et al.

[11] Patent Number: 6,103,891
[45] Date of Patent: *Aug. 15, 2000

[54] METHOD FOR THE SYNTHESIS OF NUCLEOTIDE OR OLIGONUCLEOTIDE PHOSPHORAMIDITES

[75] Inventors: Richard H. Griffey, Vista; Douglas L. Cole, San Diego; Vasulinga T. Ravikumar, Carlsbad, all of Calif.

[73] Assignee: Isis Pharmaceuticals, Inc., Carlsbad, Calif.

[*] Notice: This patent is subject to a terminal disclaimer.

[21] Appl. No.: 09/249,528

[22] Filed: Feb. 12, 1999

Related U.S. Application Data

[63] Continuation-in-part of application No. 09/094,251, Jun. 9, 1998, abandoned, which is a continuation of application No. 08/775,019, Dec. 27, 1996, Pat. No. 5,955,600.

[51] Int. Cl.$^7$ .......................... C07H 21/02; C07H 19/10; C07H 19/20; C07H 21/04

[52] U.S. Cl. .................... 536/25.34; 536/23.1; 536/26.7; 536/26.8; 536/70

[58] Field of Search ............................... 536/23.1, 25.34, 536/26.7, 26.8; 558/70

[56] References Cited

U.S. PATENT DOCUMENTS

| | | | |
|---|---|---|---|
| 3,687,808 | 8/1972 | Merigan, Jr. et al. | 435/91.3 |
| 4,415,732 | 11/1983 | Caruthers et al. | 536/26.5 |
| 4,458,066 | 7/1984 | Caruthers et al. | 536/25.34 |
| 4,500,707 | 2/1985 | Caruthers et al. | 536/25.34 |
| 4,668,777 | 5/1987 | Caruthers et al. | 536/26.5 |
| 4,774,348 | 9/1988 | Pawloski | 558/91 |
| 5,212,295 | 5/1993 | Cook | 536/26.7 |
| 5,489,677 | 2/1996 | Sanghevi et al. | 536/22.1 |
| 5,623,070 | 4/1997 | Cook et al. | 536/27.6 |
| 5,792,844 | 8/1998 | Sanghvi et al. | 536/23.1 |

OTHER PUBLICATIONS

Ono et al., "The Synthesis of Blocked Triplett–Phosphoramidites and Their Use in Mutagenesis," *Nucleic Acids Research*, 23(22), 4677–4682 (Nov. 25, 1995).

Fourrey et al., "Preparation and Phosphorylation Reactivity of N–Nonacylated Nucleoside Phosphoramidites," *Tetrahedron Letters*, 26(22), 2663–2666 (1985).

Beaucage et al., "Advances in te Synthesis of Oligonucleotides by the Phosphoramidite Method," *Tetrahedron*, 48(12), 2223–2311 (1992).

Cook (II), "Medicinal Chemistry of Antisense Oligonucleotides," *Anti–Cancer Drug Design*, 6, 585–607 (1991).

Delgardo et al., "The Uses and Properties of PEG–Linked Proteins," *Critical Reviews in Therapeutic Drug Carrier Systems*, 9(3–4), 249–304 (1992).

De Mesmaeker et al. (I), "Amides as Substitute for the Phosphodiester Linkage in Antisense Oligonucleotides," *Synlett.*, 10, 733–736 (Oct. 1993).

De Mesmaeker et al. (II), "Comparison of Rigid and Flexible Backbones in Antisense Oligonucleotides," *Bioorganic Medicinal Chemistry Letters*, 4(3), 395–398 (1994).

De Mesmaeker et al. (III), "Replacement of the Phosphodiester Linkage in Oligonucleotides: Comparison of Two Structural Amide Isomers," *Bioorganic Medicinal C Letters*, 4(7), 873–878 (1994).

*Oligonucleotides and Analogs: A Practical Approach*, Eckstein (ed.), 1991, IRL Press, Oxford, UK.

Englisch et al., "Chemically Modified Oligonucleotides as Probes and Inhibitors," *Angew. Chemie Intl. Ed. English*, 30(6), 613–629 (Jun. 1991).

Hotoda et al., "Tris(2,4,6–Tribromophenoxy) Dichlorophosphorane: A Novel Condensing Agent for Rapid Internucleotidic Bond Formation in the Phosphotriester Approach," *Tetrahedron Letters*, 28(15), 1681–1684 (1987).

*Concise Encyclopedia of Polymer Science and Engineering*, Kroschwitz (ed.), John Wiley & Sons, New York, NY, 1990, only pp. 858–859 supplied.

Lebreton et al. (I), "Synthesis of Thymidine Dimer Derivatives Containing and Amide Linkage and Their Incorporation Into Oligodeoxyribonucleotides," *Tetrahedron Letters*, 34(40), 6383–6386 (1993).

Lebreton et al. (II), "Comparison of Two Amides a Backbone Replacement of the Phosphodiester Linkage in Oligodeoxyribonucleotides," *Tetrahedron Letters*, 35(29), 5225–5228 (1994).

Lebreton et al. (III), "Antisense Oligonucleotides with Alternating Phosphodiester–5'–Amide–3' Linkages," *Synlett.*, 2, 137–140 (Feb. 1994).

Ouchi et al., "Synthesis and Antitumor Activity of Poly(Ethylene Glycol)s Linked to 5–Fluorouracil Via a Urethane or Urea Bond," *Drug Design and Discovery*, 9, 93–105 (1992).

Ravasio et al., "Selective Hydrogenation Promoted by Copper Catalysis. 1. Chemoselectivity, Regioselectivity, and Stereoselectivity in the Hydrogenation of 3–Substituted Steroids," *J. Organic Chemistry*, 56(13), 4329–4333 (1991).

Secrist et al., "Abstract 21," *Program and Abstracts, Tenth International Roundtable, Nucleosides, Nucleotides and Their Biological Applications*, Park City, Utah, Sep. 16, 1992.

Sanghvi, "Heterocyclic Base Modifications in Nucleic Acids and Their Applications in Antisense Oligonuceotides," Chapter 15 in *Antisense Research and Applications*, Crooke et al. (eds.), CRC Press, Boca Raton, FL, 1993, only pp. 273–288 supplied.

Scremin et al., "Stepwise Regeneration and Recovery of Deoxyribonucleoside Phosphoramidites Monomers During Solid–Phase Oligonucleotide Synthesis," *J. Organic Chemistry*, 59(8), 1963–1966 (1994).

Uhlmann et al., "Antisense Oligonucleotides: A New Therapeutic Principle," *Chemical Reviews*, 90(4), 543–584 (Jun. 1990).

(List continued on next page.)

*Primary Examiner*—Gary Geist
*Assistant Examiner*—L. Eric Crane
*Attorney, Agent, or Firm*—Woodcock Washburn Kurtz Mackiewicz & Norris LLP

[57] ABSTRACT

The present invention presents novel methods for recovery of phosphoramidites from the waste products of oligonucleotide synthesis. The methods include reacting a trihalophenoxydihalophosphorane with a H-phosphonate in the presence of an amine.

23 Claims, No Drawings

OTHER PUBLICATIONS

Wada et al. (I), "Nonoxidative Chlorination of Dialkyl Phosphonates to Dialkyl Phosphorochloridites. A New Approach to Oligonucleotide Synthesis," *J. Organic Chemistry*, 56(3), 1243–1250 (1991).

Wada et al. (II), "Nucleoside 3'-N, N'-Dialkylphosphonamidates as Novel Nucleotide Units for the Solution–Phase Oligonucleotide Synthesis," *Tetrahedron*, 49(10), 2–43–2054 (1993).

Waldner et al. (I), "Ureas as Backbone Replacements for the Phosphodiester Linkage in Oligonucleotides," *Synlett.*, 1, 57–61 (Jan. 1994).

Waldner et al. (II), "Synthesis of Oligodeoxyribonucleotides Containing Dimers with Carbamate Moieties as Replacement for the Natural Phosphodiester Linkage," *Bioorganic Medicinal Chemistry Letters*, 4(3), 405–408 (1994).

Wolfgang, "Facile Methods to Recycle Nucleosides During Solid Phase Synthesis of Oligonucleotides," *Tetrahedron Letters*, 35(19), 3041–3044 (1994).

Beaucage, S.L. et al., "Deoxynucleoside Phosphoramidites—A New Class of Key Intermediates for Deoxypolynucleotide Synthesis", *Tetrahedron Letts.*, 1981, 22, 1859–1862 (Issue No. 20).

Corio et al., "Relative Electron Densities in Substituted Benzenes", *J. Am. Chem. Soc.*, 1956, 78, 3043–3048 (Jul. 5, 1956).

Cotton et al., *Advanced Inorganic Chemistry*, 3rd Edition, John Wiley & Sons, New York, 1972, p. 375.

Fearon et al., "Investigation of the 'n–1' impurity in phosphorothioate oligodeoxynucleotides synthesized by the solid–phase β–cyanoethyl phosphoramidite method using stepwise sulfurization", *Nucl. Acids Res.*, 1995, 23(14), 2754–2761.

Hawley (ed.), *The Condensed Chemical Dictionary*, 10th Edition, Van Nostrand Reinhold Co., New York, 1981, 811–812.

Hotoda et al., "Pre–activation strategy for oligodeoxyribonucleotide synthesis using triaryloxydichloro–phosphoranes in the phosphotriester method", *Nucl. Acids. Res.*, 1989, 17(13), 5291–5305.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.*, 1990, 55, 4693–4699 (Issue No. 15).

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Kumar, G. et al., "Improvements in Oligodeoxyribonucleotide Synthesis: Methyl N,N–Dialkylphosphoramidite Dimer Units for Solid Support Phosphite Methodology", *J. Org. Chem.*, 1984, 49, 4905–4912 (Issue No. 25).

Marugg, J.E. et al., "Synthesis of phosphorothioate–containing DNA fragments by a modified hydroxybenzotriazole phosphotriester approach," *Nucl. Acids Res.*, 1984, 12, 9095–9110 (Issue No. 23).

Miura, K. et al., "Blockwise Mechanical Synthesis of Oligonucleotides by the Phosphoramidite Method", *Chem Pharm. Bull.*, 1987, 35, 833–836 (Iss. No. 2).

Ravikumar et al., "Large–Scale Synthesis of Oligodeoxyribonucleotide Phosphorothioate Using Controlled–Pore Glass as Support", *Nucleosides Nucleotides*, 1995, 14(6), 1219–1226.

Temsamani et al., "Sequence identity of the n–1 product of a synthetic oligonucleotide", *Nucl. Acids. Res.*, 1995, 23(11), 1841–1844.

Wolter, A. et al., "Polymer Support Oligonucleotide Synthesis XX: Synthesis of a Henhectacosa Deoxynucleotide by use of a Dimeric Phosphoramidite", *Nucleosides Nucleotides*, 1986, 5, 65–77.

METHOD FOR THE SYNTHESIS OF NUCLEOTIDE OR OLIGONUCLEOTIDE PHOSPHORAMIDITES

CROSS REFERENCE TO RELATED APPLICATIONS

This is a continuation in part of U.S. Ser. No. 09/094,251, filed Jun. 9, 1998, now abandoned, which is a continuation of U.S. Ser. No. 08/775,019, filed Dec. 27, 1996, now U.S. Pat. No. 5,955,600 the disclosure of which is hereby incorporated by reference in its entirety.

FIELD OF THE INVENTION

This invention is directed to novel methods for the preparation of phosphoramidites and oligophosphoramidites. The methods are useful, inter alia, for the preparation of phosphoramidites which are useful, in turn, in the synthesis of oligonucleotide diagnostic reagents, research reagents and therapeutics agents. In preferred embodiments, the synthetic method comprises preparation of dihalophosphoranes bearing halogen-substituted, phenoxy-containing moieties, and especially tris (halophenoxy)-dihalophosphoranes.

BACKGROUND OF THE INVENTION

It is well known that most of the bodily states in mammals, including most disease states, are affected by proteins. Such proteins, either acting directly or through their enzymatic functions, contribute in major proportion to many diseases in animals and man. Classical therapeutics has generally focused on interactions with such proteins in efforts to moderate their disease causing or disease potentiating functions. Recently, however, attempts have been made to moderate the actual production of such proteins by interactions with molecules that direct their synthesis, such as intracellular RNA. By interfering with the production of proteins, it has been hoped to affect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another.

Prior attempts at antisense therapy have provided oligonucleotides or oligonucleotide analogs that are designed to bind in a specific fashion to a specific mRNA by hybridization (i.e., oligonucleotides that are specifically hybridizable with a target mRNA). Such oligonucleotides and oligonucleotide analogs are intended to inhibit the activity of the selected mRNA by any of a number of mechanisms, i.e., to interfere with translation reactions by which proteins coded by the mRNA are produced. The inhibition of the formation of the specific proteins that are coded for by the mRNA sequences interfered with have been hoped to lead to therapeutic benefits; however there are still problems to be solved. See generally, Cook, P. D. *Anti-Cancer Drug Design* 1991, 6,585; Cook, P. D. *Medicinal Chemistry Strategies for Antisense Research*, in *Antisense Research & Applications*, Crooke, et al., CRC Press, Inc.; Boca Raton, Fla., 1993; Uhlmann, et al., A. Chem. Rev. 1990, 90, 543.

Oligonucleotides and oligonucleotide analogs are now accepted as therapeutic agents holding great promise for therapeutics and diagnostics methods. But applications of oligonucleotides and oligonucleotide analogs as antisense agents for therapeutic purposes, diagnostic purposes, and research reagents often require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides and oligonucleotide analogs toward nuclease degradation.

A serious deficiency of unmodified oligonucleotides for these purposes, particularly antisense therapeutics, is the enzymatic degradation of the administered oligonucleotides by a variety of intracellular and extracellular ubiquitous nucleolytic enzymes.

A number of chemical modifications have been introduced into antisense agents (i.e., oligonucleotides and oligonucleotide analogs) to increase their therapeutic activity. Such modifications are designed to increase cell penetration of the antisense agents, to stabilize the antisense agents from nucleases and other enzymes that degrade or interfere with their structure or activity in the body, to enhance the antisense agents' binding to targeted RNA, to provide a mode of disruption (terminating event) once the antisense agents are sequence-specifically bound to targeted RNA, and to improve the antisense agents' pharmacokinetic and pharmacodynamic properties. It is unlikely that unmodified, "wild type," oligonucleotides will be useful therapeutic agents because they are rapidly degraded by nucleases.

Potential applications of these oligonucleotides and their modified derivatives as drugs have created new challenges in the large-scale synthesis of these compounds.

The solid phase synthesis of oligonucleotides is inherently wasteful in that more than one equivalent of nucleosidic phosphoramidite synthons is used presumably to drive the reaction to completion. Given the vast amounts of oligonucleotide syntheses performed for research use and for large scale manufacture pursuant to clinical trials, the waste of expensive nucleoside phosphoramidites is a significant economic and ecological problem. This problem becomes more acute if one has to synthesize the monomer through a multistep synthesis before reaching the phosphoramidite stage, as is the case where modified sugar or nucleobase containing synthons are used in oligonucleotide therapeutic agents.

Consequently, there remains a need in the art for synthetic methods which do not require the sacrifice of large amount of phosphoramidite reagent.

The large-scale synthesis of oligonucleotide phosphorothioates can be carried out by initial formation of an internucleotidic phosphite linkage employing phosphoramidite chemistry, followed by sulfurization of the phosphite to a phosphorothioate employing a Beaucage reagent. See, e.g., Beaucage et al., *Tetrahedron Lett.*, 1981, 22, 1859; Iyer et al., *J. Org. Chem.*, 1990, 55, 4693; Iyer et al., *J. Am. Chem. Soc.*, 1990, 112, 1253; Beaucage et al., *Tetrahedron*

*Lett.*, 1992, 48, 2223; Ravikumar et al., *Nucleosides Nucleotides*, 1995, 14, 1219. Nucleoside beta-cyanoethyl phosphoramidite is the most widely employed monomer synthon for this purpose, providing coupling yields of up to 98.5% with as little as a 1.5-fold molar excess of the amidite.

However, problems are commonly encountered in the automated synthesis of the oligonucleotide phosphodiesters and phosphorothioates by way of the aforementioned phosphoramidite monomer approach. One such problem is the formation of a population of shorter (deletion or failure) sequences, within which one or more intended nucleotides are absent. See, e.g., Temsamani et al., *Nucleic Acids Res.*, 1995, 23, 1841; Fearson et al., *Nucleic Acids Res.*, 1995, 23, 2754. The purification procedures which are routinely employed to remove deletion sequences are not 100% effective, and they fail to eliminate all impurity populations. Therefore, the final purified oligonucleotide phosphorothioate product may be contaminated with n-1 length deletion sequences, and to some extent n-2 and n-3 deletion sequences.

The formation of deletion sequences is believed to be due, in part, to inefficiency of coupling. One strategy to increase the coupling efficiency is the use of a blockmer coupling strategy, in which the coupled synthon contains two or more linked nucleotide units. See, e.g., Kumar et al., *J. Org. Chem.*, 1984, 49, 4905; Marugg et al., *Nucleic Acids Res.*, 1984, 12, 9095; Wolter et al., *Nucleosides Nucleotides*, 1986, 5, 65; Miura et al., *Chem. Pharm. Bull.*, 1987, 35, 833. More recently, it has been demonstrated that the use of dimers can reduce the formation of deletion sequences in the oligonucleotide phosphorothioate product.

One method for synthesis of oligonucleotide phosphorothioate blockmers uses an excess of tris(2,4,6-tribromophenoxy)dichlorophosphorane. Hotoda et al., *Tetrahedron Lett.*, 1987, 28, 1681; Hotoda et al., *Nucleic Acid Res.*, 1989, 17, 5291; Wada et al., *J. Org. Chem.*, 56, 1243; Wada et al., *Tetrahedron*, 1993, 49, 2043. However, the reported yields of tris(2,4,6-tribromophenoxy)dichlorophosphorane could not be reproduced by the present inventors.

There remains a need in the art for synthetic methods which do not require the sacrifice of large amount of phosphoramidite reagent, and in particular, methods providing dihalophosphoranes in improved yields would further improve the efficiency of production of oligonucleotides and oligonucleotide analogs.

The present invention addresses these, as well as other important ends.

SUMMARY OF THE INVENTION

The present invention is directed to novel methods for the recovery of phosphoramidites from waste products of traditional phosphoramidite synthesis. In preferred embodiments, methods are provided for the preparation of phosphoramidites comprising the steps of:

reacting a compound of formula I or II:

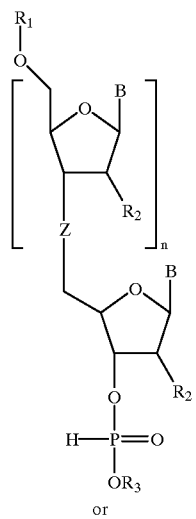

or

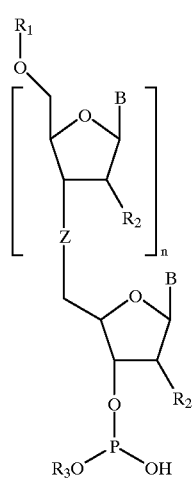

wherein:
  Z is an intersugar linkage;
  $R_1$ is a hydroxyl protecting group;
  $R_2$ is H, OH, O-alkyl, O-alkylamino, O-alkylalkoxy, a polyether of formula (O-alkyl), where m is 1 to about 10, or a protected hydroxyl group;
  $R_3$ is a phosphoryl protecting group;
  B is a nucleobase; and
  n is 0 to about 100;
with a (halophenoxy)dihalophosphorane of formula:

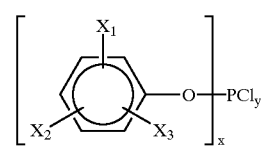

wherein:
  $X_1$ is Br or Cl;
  $X_2$ and $X_3$ are, independently, H, Br or Cl;
  x and y are each, independently, 2 or 3, and the sum of x and y is 5; and contacting the product of the reaction with a compound of formula $HN(Q)_2$ to yield a phosphoramidite of formula:

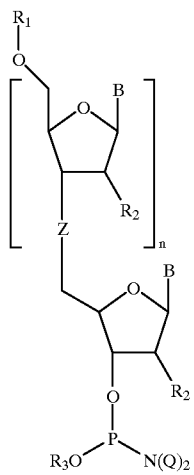

wherein each Q is independently alkyl having from 1 to 15 carbons, aryl having from 6 to 14 carbons or can form a heterocyclic ring having from 2 to 10 carbons with the nitrogen of the phosphoramidite;

wherein said (halophenoxy)dihalophosphorane is prepared by the steps of:
(a) reacting a halophenoxy compound with a phosphorus trihalide for a time and under conditions sufficient to prepare a (halophenoxy)phosphite; and
(b) contacting said (halophenoxy)phosphite with a halogen reagent for a time and under conditions sufficient to prepare said (halophenoxy) dihalophosphorane.

In some preferred embodiments of the methods of the invention, Q is alkyl, preferably isopropyl. In further preferred embodiments of the methods of the invention, $R_3$ is cyanoethyl, 4-cyano-2-butenyl, or diphenylmethylsilylethyl.

In some preferred embodiments, x is 2 and y is 3. In other preferred embodiments, x is 3 and y is 2.

In some preferred embodiments of the methods of the invention, the reaction of said compound of Formula I or II with said (halophenoxy)dihalophosphorane is preformed in an organic solvent, preferably acetonitrile.

In some preferred embodiments, the nucleobase is adenine, guanine, cytosine, thymine, uracil, 5-methyl cytosine or a protected derivative thereof.

In some preferred embodiments of the methods of the invention, Z is a phosphodiester linkage, a phosphorothioate linkage, a phosphorodithioate linkage; or a phosphonate linkage, with phosphodiester or phosphorothioate linkages being preferred.

Preferably, $R_3$ is cyanoethyl or 4-cyano-2-butenyl.

In some preferred embodiments of the methods of the invention, $X_1$, $X_2$ and $X_3$ are Br located at the 2-, 4- and 6-positions of the phenyl ring of said (halophenoxy) dihalophosphorane.

In further preferred embodiments of the methods of the invention, said reaction of said halophenoxy compound with said phosphorus trihalide is performed in an aromatic hydrocarbon solvent in the presence of a proton acceptor. Preferably the proton acceptor is pyridine, and the aromatic hydrocarbon solvent is benzene, toluene, or a mixture thereof.

Some preferred embodiments of the methods of the invention further comprise purifying said (halophenoxy) phosphite by heating, preferably boiling, said (halophenoxy) phosphite in the presence of a volatile organic ester compound which is preferably ethylacetate.

In some preferred embodiments of the methods of the invention, said halogen reagent is selected from the group consisting of an elemental halogen, a binary mixed halide, and mixtures thereof, with chlorine being preferred.

In some preferred embodiments of the methods of the invention, said (halophenoxy)phosphite is contacted with said halogen reagent in the presence of a halogenated alkane solvent, preferably chloroform.

In some especially preferred embodiments, said halophenoxy compound is 2,4,6-tribromophenol, and said (halophenoxy)dihalophosphorane is tris(2,4,6-tribromophenoxy)dichlorophosphorane.

In some preferred embodiments of the methods of the invention, said phosphorus trihalide is phosphorus trichloride.

In further preferred embodiments of the methods of the invention, said (halophenoxy)phosphite is tris(2,4,6-tribromophenoxy)-phosphite.

$R_2$ is preferably H, a protected hydroxyl group, O-alkyl or O-alkylalkoxy. In more preferred embodiments $R_2$ is methoxyethoxy.

DETAILED DESCRIPTION OF PREFERRED EMBODIMENTS

The present invention presents novel methods for the preparation of phosphoramidites. The methods are useful for the recovery of a wide variety of species produced as waste products in oligonucleotide synthesis. In preferred embodiments, methods are provided for the preparation of phosphoramidites of formula:

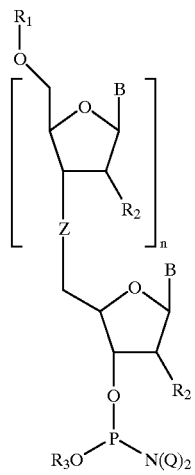

wherein Z is an internucleoside linkage; $R_1$ is a hydroxyl protecting group; $R_2$ is H, OH, O-alkyl, O-alkylamino, O-alkylalkoxy, a polyether of formula $(O\text{-alkyl})_m$ where m is 1 to about 10, or a protected hydroxyl group; $R_3$ is a phosphoryl protecting group; B is a nucleobase; n is 0 to about 100, and each Q is independently alkyl having from 1 to 15 carbons, aryl having from 6 to 14 carbons, or $(Q)_2$ together with the phosphoamidite nitrogen can form a heterocyclic ring having from 2 to 10 carbons. The methods include the steps of:

reacting a compound of formula I or II:

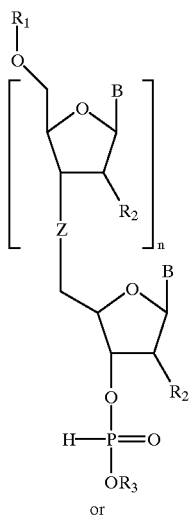

or

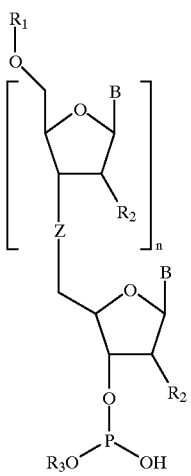

wherein:
Z is an intersugar linkage;
$R_1$ is a hydroxyl protecting group;
$R_2$ is H, OH, O-alkyl, O-alkylamino, O-alkylalkoxy, a polyether of formula (O-alkyl)$_m$ where m is 1 to about 10, or a protected hydroxyl group;
$R_3$ is a phosphoryl protecting group;
B is a nucleobase; and
n is 0 to about 100;
with a (halophenoxy)dihalophosphorane of formula:

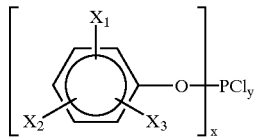

wherein:
$X_1$ is Br or Cl;
$X_2$ and $X_3$ are, independently, H, Br or Cl;
x and y are each, independently, 2 or 3, and the sum of x and y is 5; and contacting the product of the reaction with a compound of formula $HN(Q)_2$ to yield a phosphoramidite of formula:

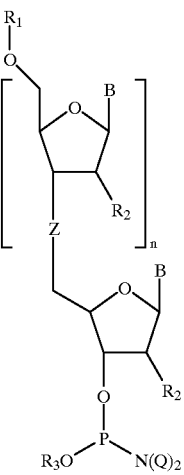

wherein each Q is independently alkyl having from 1 to 15 carbons, aryl having from 6 to 14 carbons or can form a heterocyclic ring having from 2 to 10 carbons with the nitrogen of the phosphoramidite;
wherein said (halophenoxy)dihalophosphorane is prepared by the steps of:
(a) reacting a halophenoxy compound with a phosphorus trihalide for a time and under conditions sufficient to prepare a (halophenoxy)phosphite; and
(b) contacting said (halophenoxy)phosphite with a halogen reagent for a time and under conditions sufficient to prepare said (halophenoxy) dihalophosphorane.

Compounds of Formula I or II can derive from the waste excess phosphoramidite reagents used in traditional oligonucleotide synthesis, as described in, for example, *Oligonucleotides and Analogues: A Practical Approach*, Eckstein, F., Ed., IRL Press, Oxford, U.K. 1991, which is incorporated herein by reference in its entirety. In a typical oligonucleoide synthetic regime, the free 5-hydroxyl of the growing oligonucleotide chain is reacted with a several-fold molar excess of nucleoside N,N-dialkylphosphoramidite in the presence of excess tetrazole. It is believed that the tetrazole catalyst first displaces the secondary amino group of the phosphoramidite to form a tetrazolide adduct. The tetrazolide then reacts with the free 5'-hydroxyl of the growing chain to form a phosphite, which is subsequently transformed into the desired linkage by, for example, oxidation. The excess (i.e., unreacted) terazolide adduct is washed from the reaction chamber, and subsequently reacts with ambient water to form an H-phosphonate species represented by Formula I, which exists in equilibrium with its tautomer, represented by Formula II. Thus, in one aspect, the present invention provides a convenient method of recovering phosphoramidite synthons from waste products of oligonucleotide synthesis.

The methods of the present invention provide significant economic and ecological benefits in oligonucleotide synthesis. While not wishing to be bound by a particular theory, it is believed that the phosphonate species (Formula I) and its phosphite tautomer (Formula II) exist in equilibrium in solution, with the phosphonate species being heavily favored. The halophenoxychlorophosphorane, preferably tris(2,4,6-tribromophenoxy) dichlorophosphorane or bis[2,4,6-tribromophenoxy] trichlorophosphorane, is believed to preferentially react with the phosphite species to form a halide adduct, which then reacts with a secondary amine to form the phosphoramidite product. Accordingly, the methods of the present invention can be conveniently performed in a single reaction container, or in stages.

The synthons of Formula I or II are derived from any of the wide variety of phosphoramidite species capable of being used in phosphoramidite ologomer synthesis. Accordingly, the synthons can be monomeric, dimeric, or higher order synthons (i.e., oligophosphoramidites), and can comprise any of the wide variety of internucleoside linkages, sugars, nucleobases, and modified derivatives thereof known in the art.

Examples of internucleoside linkages which can be present in synthons of Formula I or II include phosphodiester, phosphorothioate, phosphorodithioate, and phosphonate linkages. Further representative internucleotide linkages include amide or substituted amide linkages, such as those described in Waldner et al., *Synlett.* 1, 57–61 (1994), De Mesmaeker et al., *Synlett.* 10, 733–736 (1993), Lebreton et al., *Synlett.* 2, 137–140 (1994), De Mesmaeker et al., *Bioorg. Medic. Chem. Lett.* 4, 395–398 (1994), De Mesmaeker et al., *Bioorg. Medic. Chem. Lett.* 4, 873–878 (1994), Lebreton et al., *Tet. Letters* 34, 6383–6386 (1993), Lebreton et al., *Tet. Letters* 35, 5225–5228 (1994), Waldner et al., *Bioorg. Medic. Chem. Lett.* 4, 405–408 (1994), and linkages described in U.S. Pat. No. 5,489,677, U.S. Ser. No. 08/317, 289, filed Oct. 3, 1994, U.S. Ser. No. 08/395,168, filed Feb. 27, 1995.

In the context of the present invention, the term "oligonucleotide" refers to a plurality of joined nucleotide units formed in a specific sequence. The term nucleotide has its accustomed meaning as the phosphoryl ester of a nucleoside. The term "nucleoside" also has its accustomed meaning as a pentofuranosyl sugar which is bound to a nucleosidic base (i.e., a nitrogenous heterocyclic base or "nucleobase").

It will be appreciated that the methods of the present invention can be used for the synthesis of phosphoramidites having both naturally occurring and non-naturally occurring constituent sugars, internucleoside linkages and/or nucleobases (i.e., nucleosidic bases). Non-naturally occurring sugars, internucleoside linkages and nucleobases are typically structurally distinguishable from, yet functionally interchangeable with, naturally occurring sugars (e.g. ribose and deoxyribose), internucleoside linkages (i.e. phosphodiester linkages), and nucleosidic bases (e.g., adenine, guanine, cytosine, thymine). Thus, non-naturally occurring moieties include all such structures which mimic the structure and/or function of naturally occurring moiety, and which aid in the binding of the oligonucleotide analog to a target, or otherwise advantageously contribute to the properties of the phosphorothioate oligomer.

Representative examples of non-naturally occurring sugars include sugars having any of a variety of substituents attached to their 2'-positions. These include, for example, halides, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, the disclosure of which is hereby incorporated by reference.

Sugars having O-substitutions on the ribosyl ring are also amenable to the present invention. Representative substitutions for ring O include S, $CH_2$, CHF, and $CF_2$, see, e.g., Secrist, et al., Abstract 21, *Program & Abstracts, Tenth International Roundtable, Nucleosides, Nucleotides and their Biological Applications,* Park City, Utah, Sep. 16–20, 1992.

Representative nucleobases suitable for use in the methods of the invention include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), by Sanghvi, Y., in chapter 15 of *Antisense Research and Application,* Ed. S. T. Crooke and B. Lebleu, CRC Press, 1993, in Englisch et al., *Angewandte Chemie,* International Edition, 1991, 30, 613–722 (see especially pages 622 and 623), in the *Concise Encyclopedia of Polymer Science and Engineering,* J. I. Kroschwitz Ed., John Wiley & Sons, 1990, pages 858–859, and in Cook, P. D., *Anti-Cancer Drug Design,* 1991, 6, 585–607. The disclosures of each of the foregoing is incorporated by reference in their entirety. The terms "nucleosidic base" and "nucleobase" are further intended to include heterocyclic compounds that can serve as nucleosidic bases, including certain 'universal bases' that are not nucleosidic bases in the most classical sense, but function similarly to nucleosidic bases. One representative example of such a universal base is 3-nitropyrrole.

In some preferred embodiments of the invention $R_1$ is a hydroxyl protecting group. A wide variety of hydroxyl protecting groups can be employed in the methods of the invention. Preferably, the protecting group is stable under basic conditions but can be removed under acidic conditions. Representative hydroxyl protecting groups are disclosed by Beaucage, et al., *Tetrahedron* 1992, 48, 2223–2311, and also in e.g., Green and Wuts, Protective Groups in Organic Synthesis, 2d edition, John Wiley & Sons, New York, 1991 at Chapter 2. Preferred protecting groups used for $R_1$ include dimethoxytrityl (DMT), monomethoxytrityl, 9-phenylxanthen-9-yl (Pixyl) and 9-(p-methoxyphenyl)xanthen-9-yl (Mox). The $R_1$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide.

In some preferred embodiments of the invention $R_3$ is a phosphoryl protecting group. The phosphoryl protecting group is attached to the phosphorus-bound oxygen, and serves to protect the phosphorus during oligonucleotide synthesis. See *Oligonucleotides and Analogues: A Practical Approach,* supra. One representative phosphoryl protecting group is the cyanoethyl group. Other representative phosphoryl protecting groups include 4-cyano-2-butenyl groups, methyl groups, and diphenylmethylsilylethyl (DPSE) groups.

In general, protecting groups are used in the oligonucleotide synthetic methods of the invention for protection of several different types of functionality. In general, protecting groups render chemical functionality inert to specific reaction conditions and can be appended to and removed from such functionality in a molecule without substantially damaging the remainder of the molecule. Representative protecting groups useful to protect nucleotides during phosphorothioate synthesis include base labile protecting groups and acid labile protecting groups. Base labile protecting groups are used to protect the exocyclic amino groups of the heterocyclic nucleobases. This type of protection is generally achieved by acylation. Two commonly used acylating groups are benzoylchloride and isobutyrylchloride. These protecting groups are stable to the reaction conditions used in the methods of the invention, and during oligonucleotide synthesis, and are cleaved at approximately equal rates during the base treatment at the end of oligonuclotide synthesis. The second type of protection, also used in the synthetic methods of the invention, is an acid labile protecting group, which is used to protect the nucleotide 5'-hydroxyl during synthesis.

In the methods of the present invention, the product of the reaction between the compound of Formula I or II and the tribromophenoxychlorophosphorane reacts with a secondary amine to form the phosphoramidite product. The substituents of the secondary amine can be chosen from among the many species that are know to function as phosphoramidite nitrogen substituents. Representative examples include lower alkyl groups, aryl groups, and cyclic structure such as where the phosphoramidite nitrogen forms part of a N-morpholine ring system. In particularly preferred embodiments the substituents are lower alkyl groups, especially isopropyl groups. Other examples of suitable amines as are described in various U.S. patents, principally those to M. Caruthers and associates. These include U.S. Pat. Nos. 4,668,777; 4,458,066; 4,415,732; and 4,500,707; all of which are herein incorporated by reference.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

In some preferred embodiments of the invention amino groups are appended to alkyl or other groups, such as, for example, 2'-alkoxy groups (e.g., where $R_2$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Chapter 7 of Greene and Wuts, supra. Generally, as used herein, the term "nucleobase" includes protected derivatives thereof.

Oligomer phosphoramidites produced by the methods of the invention will preferably comprise from about 1 to about 100 monomer subunits. It is more preferred that such compounds comprise from about 1 to about 30 monomer subunits, with 1 to 10 monomer subunits being more preferred, and 1 to 5 monomer subunits being particularly preferred.

Tris[2,4,6-tribromophenoxy]dichlorophosphorane or bis[2,4,6-tribromophenoxy]trichlorophosphorane can be synthesized according to the method of Hotoda et al., Tetrahedron Letters 1987 28 (15) 1681–1684.

However, in preferred embodiments, the methods of the present invention include the steps of reacting a halophenoxy compound with a phosphorus trihalide compound in amounts and under reaction conditions sufficient to form a (halophenoxy)phosphite. The (halophenoxy)phosphite is contacted with a halogen reagent in amounts and under reaction conditions sufficient to form a (halophenoxy)halophosphorane.

In one embodiment of the present invention the halophenoxy compound is a halogen substituted phenoxy compound of the formula:

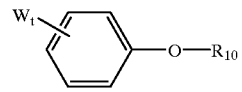

III wherein:
each W is an independently selected halogen;
t is an integer from 1 to 5; and
$R_{10}$ is hydrogen or $C_1$–$C_8$ alkyl.

In a preferred embodiment of the present invention each W is bromine or chlorine and the value of t is from 2 to 4. In a more preferred embodiment of the invention W is chlorine and t is from 2 to 4. In a particularly preferred embodiment, W is chlorine and t is 3. Preferably, $R_{10}$ is hydrogen.

Exemplary phosphorous trihalide compounds suitable for use in the present invention include phosphorus tribromide, phosphorus trichloride, and mixed bromide/chlorides. A preferred phosphorus trihalide is phosphorus trichloride.

As used herein, the term (halophenoxy)phosphite denotes a trivalent phosphorus compound containing phosphorus substituted with a residue of the precursor halo-substituted phenoxy compound. Preferred (halophenoxy)phosphite compounds have the following general formula:

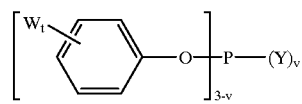

IV wherein W and t are as defined above, v is 0, 1 or 2, and Y is a halogen.

In some particularly preferred embodiments, Y is bromine or chlorine. In more preferred embodiments, the compound is a tris(halophenoxy)phosphite (i.e., v=0).

Preferred halogen reagents for use in the processes of the present invention include elemental halogens and mixed bihalogen compounds such as, for example, elemental bromine or chlorine, the binary halide BrCl, and mixtures thereof. Chlorine is especially preferred.

As used herein, the term (halophenoxy) dihalophosphorane denotes a pentavalent organophosphorus compound derived from a (halophenoxy)phosphite, and having two additional halide moieties bonded to the pentavalent phosphorus. In preferred embodiments, the methods of the present invention utilize (halophenoxy) dihalophosohorane compounds of the formula (V):

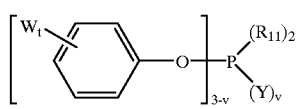

wherein W, t, v, and Y are as defined above; and $R_{11}$ is halogen.

$R_{11}$ is preferably independently chlorine or bromine. More preferably, both $R_{11}$ are chlorine. A particularly preferred compound of Formula V is a tris(halophenoxy) dihalophosphorane having three halophenoxy moieties (i.e., v is 0) and wherein the $R_{11}$ groups are both chlorine, and all W groups are bromine.

In accordance with preferred embodiments of the methods of the invention, the halophenoxy compound and the phosphorus trihalide are reacted under conditions and for a time sufficient to yield a (halophenoxy)phosphite. See, e.g., Pawloski, U.S. Pat. No. 4,774,348; Hawley (Ed.), "The Condensed Chemical Dictionary," 10th Ed., 1981, Van Nostrand Reinhold Co., New York, pages 811–12 (phosphorus tribromide, trichloride, triiodide); Cotton et al., "Advanced Inorganic Chemistry," 3rd Ed., 1972, John Wiley & Sons, New York, page 375.

The halophenoxy compound and the phosphorous trihalide can be reacted, if desired, in the presence of one or more diluents or solvents, which are preferably inert. For example, the solvent may be an aromatic liquid such as an aromatic hydrocarbon. Exemplary suitable aromatic hydrocarbons are benzene, toluene, and the like. The appropriate amount of diluent or solvent can be readily determined by one of skill in the art.

In preferred embodiments, an acceptor for the group "R" can be employed. Preferably, one equivalent or greater of acceptor is used for each equivalent of alkyl group or proton expected to be released from the halophenoxy compound. One particularly preferred acceptor is pyridine, preferably anhydrous pyridine. In some preferred embodiments, pyridine is used as a proton acceptor.

The time for which the halophenoxy compound and the phosphorous trihalide are reacted can vary from several hours. In general, the reaction is maintained for a time sufficient that the halophenoxy compound and the phosphorous trihalide react to the desired level of completion.

The temperature which is maintained during the contacting of the phosphorous trihalide and the halophenoxy compound can vary. In general, it is preferred to carry out the reaction of the halophenoxy compound and the phosphorous trihalide at the lowest temperature which will provide for the desired efficiency of reaction. For example, suitable temperatures for the contacting step can range about from about −30° C. to about 30° C. Preferably, the reaction is carried out at ambient room temperature; i.e., temperatures from about 20° C. to about 30° C., preferably about 25° C.

The pressure maintained during the contacting of the phosphorous trihalide and the halophenoxy compound can vary. Appropriate pressures to provide efficient formation of phosphite product can be readily determined by one of skill in the art. Ambient atmospheric pressures are advantageously employed. Nevertheless, reduced pressures may be employed to remove non-reactant components such as, for example, any diluent, solvent, or acceptor used during the reaction.

The phosphite product can be in the form of a residue, especially after removal of some or all of any solvent and/or acceptor. Purification of the phosphite product can be accomplished by any of a variety of procedures routinely used by those of skill in the art of synthetic organic chemistry. In some preferred embodiments, the product is purified by heating the phosphite product in an azeotrope-forming substance to remove impurities azeotropically. One representative example of such procedure is heating, preferably boiling, the phosphite product with a volatile organic ester compound such as ethyl acetate.

Contacting of the (halophenoxy)phosphite with the halogen reagent to prepare the (halophenoxy)dihalophosphorane can be done under suitable conditions known to those skilled in the art. In some preferred embodiments, the (halophenoxy)phosphite is contacted with chlorine gas according to the procedure of Rydon et al., *J. Am. Chem. Soc.*, 1956, 78, 3043.

A diluent or solvent may be employed in the preparation of the (halophenoxy)dihalophosphorane. Preferably, any diluent or solvent used is inert. For example, the solvent may be a slightly polar organic liquid such as a halogenated alkane. Suitable halogenated alkanes include chloroform and methylene dichloride. The amount of diluent can vary and appropriate amounts can be readily determined by one of skill in the art.

The time period for contacting the (halophenoxy) phosphite with the halogen reagent can vary, and appropriate times to ensure an acceptable extent of reaction can be determined by one skilled in the art. Suitable contacting times can range from several minutes to several hours or more.

Temperatures during contacting of the (halophenoxy) phosphite with the halogen reagent can vary. In general, any temperature can be used which facilitates the formation of phosphorane product. Ambient temperatures can be advantageously employed. For example, suitable temperatures can range from about 0° C. to about 50° C., and preferably the reaction is carried out at room temperature.

The pressure at which the (halophenoxyphosphite) is contacted with the halogen reagent may vary. In general, any pressure can be used which facilitates the formation of phosphorane product. Ambient atmospheric pressures are advantageously employed. Nevertheless, reduced pressures may be employed to remove any component such as a diluent or solvent.

The phosphorane product which may be in solid form, particularly after removal of solvent and/or diluent. If desired, the product may be purified.

A (halophenoxy)dihalophosphorane formed according to the processes of the present invention may be employed in preparation of an oligonucleotide or precursor thereto, or a modified oligonucleotide such as an oligophosphrothioate. For example, the (halophenoxy)dihalophosphorane may be employed as a blockmer. The further preparation may be carried out by any suitable procedure known to those skilled in the art.

Additional advantages and novel features of this invention will become apparent to those skilled in the art upon examination of the examples thereof provided below, which should not be construed as limiting the appended claims.

EXAMPLE 1

Tris(2,4,6-tribromophenoxy)phosphite

A solution of phosphorus trichloride (4.4 mL; 50 mmol; Aldrich Chemical Co.) in anhydrous benzene (30 mL) was added dropwise to a stirred solution of 2,4,6-tribromophenol (54.6 g; 165 mmol; Aldrich Chemical Co.) and anhydrous pyridine (13.4 mL; 165 mmol) in anhydrous benzene (150 mL) at a temperature of 0° C. The mixture was allowed to warm to room temperature followed by stirring for 1 hour. Pyridinium hydrochloride was removed by filtration, and the filtrate was concentrated under reduced pressure. The residue was boiled with ethyl acetate (500 mL) and cooled to room temperature. The product crystallized and the yield, after filtration and drying, was 41.6 g (85%) as colorless crystals.

Phosphorus-31 nuclear magnetic resonance (31-P NMR) spectra were taken in deuterated chloroform ($CDCl_3$) at ambient temperature on a Varian Gemini-200 79.990 MHZ spectrometer with an external capillary using 85% phosphoric acid as a reference.

31-P NMR ($CDCl_3$) δ: 147.57.

EXAMPLE 2

Tris(2,4,6-tribromophenoxy)dichlorophosphorane

Chlorine gas, dried by passage through concentrated sulfuric acid before use, was bubbled slowly through a stirred solution of tris(2,4,6-tribromophenyl)phosphite (4.0 g; 3.9 mmol) in anhydrous chloroform (40 mL) until a pale green color persisted. The solvent was removed under vacuum to yield tris(2,4,6-tribromophenyl) dichlorophosphorane as a colorless solid in quantitative yield. 31-P NMR: ($CDCl_3$) δ: −64.64.

EXAMPLE 3

Preparation of 5'-O-(4,4'dimethoxytrityl)thymidine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with 5'-O-(4,4'dimethoxytrityl)thymidine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification. $^{31}$P NMR ($CDCl_3$) 145.5, 146.1

EXAMPLE 4

Preparation of $N^2$-Isobutyryl-5'-O-(4, 4'dimethoxytrityl)-2'-deoxyguanosine-3'-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^2$-Isobutyryl-5'-(4, 4'dimethoxytrityl)-2'-deoxyguanosine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 5

Preparation of $N^6$-Benzoyl-5'-O-(4, 4'dimethoxytrityl)-2'-deoxyadenosine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^6$-Benzoyl-5'-O-(4, 4'dimethoxytrityl)-2'-deoxyadenosine- 3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 6

Preparation of $N^4$-Benzoyl-5'-O-(4, 4'dimethoxytrityl)-2'-deoxycytidine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with $N^4$-Benzoyl-5'-O-(4, 4'dimethoxytrityl)-2'-deoxycytidine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 7

2-Diphenylmethylsilylethyl-5'-(O-4,4'-dimethoxytrityl)-thymidinyl-thymidine dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethylsilylethyl-5'-(O-4,4'-dimethoxytrityl)-thymidinyl-thymidine dimer phosphonate (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 8

2-Diphenylmethylsilylethyl-5'-(O-4,4'-dimethoxytrityl)-N4-benzoyl-2'-deoxycytidinyl-thymidine dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethylsilylethyl-5'-(O-4,4'-dimethoxytrityl)-N4-benzoyl-2'-deoxycytidinyl-thymidine dimer phosphonate (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 9

2-Diphenylmethylsilylethyl-5'-(O-4,4'-dimethoxytrityl)-N2-isobutyryl-2'-deoxyguanosinyl-thymidine dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethylsilylethyl-5'-(O-4,4'-dimethoxytrityl)-N2-isobutyryl-2'-deoxyguanosinyl-thymidine diner phosphonate (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 10

2-Diphenylmethylsilylethyl-5'-(O-4,4'-dimethoxytrityl)-N6-benzoyl-2'-deoxyadenosinyl-thymidine dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethylsilylethyl-5'-(O-4,4'-dimethoxytrityl)-N6-benzoyl-2'-deoxyadenosinyl-thymidine dimer phosphonate (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 11

2-Diphenylmethylsilylethyl-5'-(O-4,4'-dimethoxytrityl)-N2-isobutyryl-2'-deoxyguanosinyl-N6-benzoyl-2'-deoxyadenosinyl dimer amidite A 250 mL two necked flask equipped with a magnetic stirrer, a gas inlet for argon, and a septum is assembled under an argon atmosphere. All glassware are dried at 120° C. for 1 hour. The flask is charged with 2-diphenylmethylsilylethyl-5'-(O-4,4'-dimethoxytrityl)-N2-isobutyryl-2'-deoxyguanosinyl-N6-benzoyl-21-deoxyadenosinyl dimer phosphonate (0.015 mole) and diisopropylamine (0.12 mole). Anhydrous acetonitrile (200 mL) is added. To this stirred mixture under argon at room temperature is added tris(2,4,6-tribromophenoxy)dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 12

Preparation of 5'-O-(4,4'dimethoxytrityl)uridine-2'-O-methoxyethyl-3'-(2- diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with 5'-O-(4,4'dimethoxytrityl) uridine-2'-O-methoxyethyl-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification. $^{31}$P NMR (CDCl$_3$) 145.5, 146.1

EXAMPLE 13

Preparation of N$^2$-Isobutyryl-5'-O-(4,4'dimethoxytrityl)-2'-O-methoxyethylguanosine-3'-O-(2-diphenylmethylsilylethyl N,N-diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with N$^2$-Isobutyryl-5'-O-(4,4'dimethoxytrityl)-2'-O-methoxyethylguanosine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 14

Preparation of N⁶-Benzoyl-5'-O-(4, 4'dimethoxytrityl)-2'-O-methoxyethyladenosine-3'- (2-diphenylmethylsilylethyl N,N- diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with N⁶-Benzoyl-5'-O-(4, 4'dimethoxytrityl)-2'-O-methoxyethyladenosine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

EXAMPLE 15

Preparation of N⁴-Benzoyl-5'-O-(4, 4'dimethoxytrityl)-2'-O-methoxyethylcytidine-3'-O- (2-diphenylmethylsilylethyl N,N- diisopropylphosphoramidite)

A 250 mL two necked flask equipped with a magnetic stirrer, a gas inlet for argon, and a septum is assembled under an argon atmosphere. All glassware are dried at 120° C. for 1 hour. The flask is charged with N⁴-Benzoyl-5'-O-(4, 4'dimethoxytrityl)-2'-O-methoxyethylcytidine-3'-O-(2-diphenylmethylsilylethylphosphonate) (0.015 mole) and diisopropylamine (0.12 mole). Anhydrous acetonitrile (200 mL) is added. To this stirred mixture under argon at room temperature is added tris(2,4,6-tribromophenoxy) dichlorophosphorane (0.225 mole). After stirring for three hours, the reaction mixture is filtered, and concentrated under reduced pressure. The crude product is purified by flash chromatography using silica gel to afford the desired product. Triethylamine (1%) is used throughout the purification.

It is intended that each of the patents, applications, printed publications, and other published documents mentioned or referred to in this specification be herein incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A synthetic method comprising the steps of: reacting a compound of formula I or II:

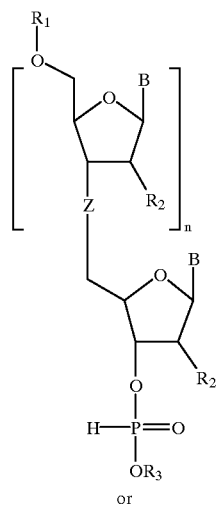

or

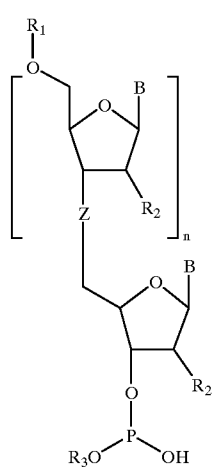

wherein:
Z is an intersugar linkage;
$R_1$ is a hydroxyl protecting group;
$R_2$ is H, OH, O-alkyl, O-alkylamino, O-alkylalkoxy, a polyether of formula (O-alkyl)$_m$ where m is 1 to about 10, or a protected hydroxyl group;
$R_3$ is a phosphoryl protecting group;
B is a nucleobase; and
n is 0 to about 100;

with a (halophenoxy)dihalophosphorane of formula:

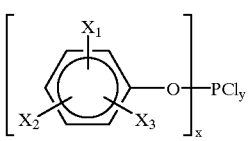

wherein:
$X_1$ is Br or Cl;
$X_2$ and $X_3$ are, independently, H, Br or Cl;
x and y are each, independently, 2 or 3, and the sum of x and y is 5; and contacting the product of the reaction with a compound of formula $HN(Q)_2$ to yield a phosphoramidite of formula:

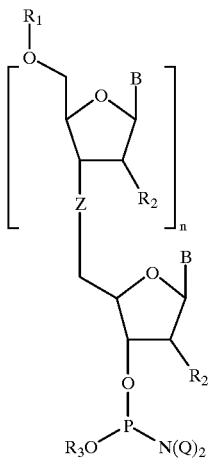

wherein each Q is independently alkyl having from 1 to 15 carbons, aryl having from 6 to 14 carbons or can form a heterocyclic ring having from 2 to 10 carbons with the nitrogen of the phosphoramidite;

wherein said (halophenoxy)dihalophosphorane is prepared by the steps of:
(a) reacting a halophenoxy compound with a phosphorus trihalide for a time and under conditions sufficient to prepare a (halophenoxy)phosphite; and
(b) contacting said (halophenoxy)phosphite with a halogen reagent for a time and under conditions sufficient to prepare said (halophenoxy) dihalophosphorane.

2. The method of claim 1 wherein Q is diisopropylamino.

3. The method of claim 1 wherein $R_3$ is cyanoethyl, 4-cyano-2-butenyl, or diphenylmethylsilylethyl.

4. The method of claim 1 wherein x is 2 and y is 3.

5. The method of claim 1 wherein x is 3 and y is 2.

6. The method of claim 1 wherein the reaction of said compound of Formula I or II with said (halophenoxy) dihalophosphorane is performed in acetonitrile.

7. The method of claim 1 wherein the nucleobase is 9-adeninyl, 9-guaninyl, 1-cytosinyl, 1-thyminyl, 1-uracilyl, 1-(5-methyl)cytosinyl or a protected derivative thereof.

8. The method of claim 1 wherein Z is a phosphodiester linkage, a phosphorothioate linkage, a phosphorodithioate linkage, or a phosphonate linkage.

9. The method of claim 8 wherein Z is a phosphodiester linkage or a phosphorothioate linkage.

10. The method of claim 1 wherein $R_3$ is cyanoethyl.

11. The method of claim 1 wherein $R_3$ is 4-cyano-2-butenyl.

12. The method of claim 1 wherein $X_1$, $X_2$ and $X_3$ are Br located at the 2-, 4- and 6-positions of the phenyl ring of said (halophenoxy)dihalophosphorane.

13. The method of claim 1 further comprising reacting said halophenoxy compound with said phosphorus trihalide in an aromatic hydrocarbon solvent in the presence of a proton acceptor.

14. The method of claim 13 wherein said proton acceptor is pyridine.

15. The method of claim 13 wherein said aromatic hydrocarbon solvent is benzene, toluene, or a mixture thereof.

16. The method of claim 13 further comprising purifying said (halophenoxy)phosphite by heating said (halophenoxy) phosphite in the presence of a volatile organic ester compound.

17. The method of claim 1 wherein said halogen reagent is selected from the group consisting of an elemental halogen, a binary mixed halide, and mixtures thereof.

18. The method of claim 1 wherein said (halophenoxy) phosphite is contacted with said halogen reagent in the presence of a halogenated alkane solvent.

19. The method of claim 1 wherein said halophenoxy compound is 2,4,6-tribromophenol.

20. The method of claim 1 wherein said phosphorus trihalide is phosphorus trichloride.

21. The method of claim 1 wherein said (halophenoxy) phosphite is tris(2,4,6-tribromophenoxy)-phosphite.

22. The method of claim 1 wherein said halogen reagent is chlorine.

23. The method of claim 1 wherein said (halophenoxy) dihalophosphorane is tris(2,4,6-tribromophenoxy) dichlorophosphorane.

* * * * *

UNITED STATES PATENT AND TRADEMARK OFFICE
CERTIFICATE OF CORRECTION

PATENT NO.    : 6,103,891
DATED         : August 15, 2000
INVENTOR(S)   : Griffey et al.

It is certified that error appears in the above-identified patent and that said Letters Patent is hereby corrected as shown below:

Column 4,
Line 48, please delete "(O-alky)," and insert therefor -- $(O\text{-alkyl})_m$ --;

Column 15,
Line 61, please delete "$N^2$-Isobutyryl-5'(4," and insert therefor -- $N^2$-Isobutyryl -5'O-(4, --;

Column 18,
Line 12, please delete "-21-" and insert therefor -- -2'- --;
Line 27, please insert -- -O- -- in between -3'(2- to read -3'-O-(2-;

Column 19,
Line 5, please insert -- -O- -- after -3'- to read -3'-O-;

Signed and Sealed this

Twenty-sixth Day of February, 2002

*Attest:*

*Attesting Officer*

JAMES E. ROGAN
*Director of the United States Patent and Trademark Office*